United States Patent [19]

Vincent

[11] Patent Number: 4,840,983
[45] Date of Patent: Jun. 20, 1989

[54] ANTI-TREEING ADDITIVES

[75] Inventor: Gary A. Vincent, Midland, Mich.

[73] Assignee: Dow Corning Corporation, Midland, Mich.

[21] Appl. No.: 866,413

[22] Filed: May 23, 1986

[51] Int. Cl.$^4$ ............................. C08K 5/04; C08K 5/54
[52] U.S. Cl. ............................. 524/265; 174/110 SR; 174/110 SY; 174/110 B; 174/110 PM; 174/110 V; 174/110 S
[58] Field of Search ................. 524/265; 124/110 SR, 124/110 SY, 110 B, 110 PM, 110 V, 110 S

[56] References Cited

U.S. PATENT DOCUMENTS

| | | | |
|---|---|---|---|
| 3,465,020 | 9/1969 | Frye | 260/448.8 |
| 3,652,484 | 3/1972 | Weissermel et al. | 524/265 |
| 3,956,420 | 5/1976 | Kato et al. | 260/827 |
| 4,114,202 | 3/1979 | Ashcraft et al. | 252/63.2 |
| 4,263,158 | 4/1981 | Ashcraft et al. | 252/573 |
| 4,299,713 | 11/1981 | Maringer et al. | 174/110 |
| 4,332,957 | 6/1982 | Braus et al. | 556/446 |
| 4,400,429 | 8/1983 | Barlow et al. | 524/265 X |
| 4,482,476 | 11/1984 | Yoshimura et al. | 524/265 X |
| 4,543,381 | 9/1985 | Barlow et al. | 524/265 X |
| 4,608,306 | 8/1986 | Vincent | 524/265 X |

FOREIGN PATENT DOCUMENTS

| | | | |
|---|---|---|---|
| 1103915 | 6/1981 | Canada | 524/265 UX |
| 2737430 | 3/1983 | Fed. Rep. of Germany | 524/265 UX |
| 92946 | 7/1981 | Japan | 524/265 UX |
| 109404 | 8/1981 | Japan | 524/265 UX |
| 1248256 | 9/1971 | United Kingdom | 524/265 UX |
| 1277378 | 6/1972 | United Kingdom | 524/265 UX |

Primary Examiner—Paul F. Shaver
Attorney, Agent, or Firm—Alexander Weitz

[57] ABSTRACT

An organosilane of the general formula

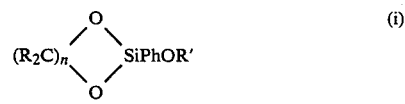

(i)

where R denotes a hydrogen or alkyl radical, n is 2 to 5, Ph denotes an aryl radical, and R' denotes an alkyl radical, and the hydrolysis product, a disiloxane, of said organosilanes with water, where said compounds are useful as anit-treeing additives to polyolefin.

7 Claims, No Drawings

ANTI-TREEING ADDITIVES

BACKGROUND OF THE INVENTION

1. Field of the Invention

This application relates to anti-treeing additives effective in polyolefin polymers. The application further relates to improved electrical insulation materials, and improved electrical cables.

This invention further relates to an electrical cable comprising a primary insulating layer manufactured from the polyethylene and the anti-treeing additive.

2. Description of the Prior Art

Polymeric compositions are well-known and are used extensively as primary insulation materials for wire and cable. As an insulator, it is important the composition have various physical and electrical properties, such as resistance to mechanical cut through; stress crack resistance; and dielectric failure. Recent publications have indicated water tree growth and electrical tree growth in the primary insulation are particularly important problems since they are associated with, though not necessarily totally responsible for, dielectric failure.

An important application for a primary insulating material is in high voltage transmission and distribution cable, especially useful in direct buried underground service. Unfortunately, the efficient use of polymeric compositions in high voltage cables is precluded by a degradation process called "treeing". Treeing is an electrical pre-breakdown process. The name is given to the damage in a solid dielectric exposed to electrical stress wherein the damage visually resembles trees. Treeing can occur and progresses as a result of partial discharges or without discharges in the presence of moisture, and with impulses, ac, or dc voltages.

It is generally believed two different types of trees exist. Trees which form in the presence of water, and in particular at low voltages, are called water or electrochemical trees. When water is absent, the trees which form are called electrical trees.

Although there are many theories concerning the initiation and growth of trees, there is virtual unanimity in the belief they start at an imperfection in the cable. This imperfection can be a small void or a piece of solid contamination.

Several organic additives have been discovered which are quite effective in retarding the growth of both types of trees. Acetophenone is perhaps one of the best known anti-treeing agents in existence. It is a product of the decomposition of dicumylperoxide which has found wide use as a curing agent to produce crosslinked polyethylene. The initial decreased treeing tendency of crosslinked polyethylene is a direct result of the existence of acetophenone in the former. Unfortunately, the effect is only temporary because the acetophenone diffused out of the polyethylene with time; and the polymer's resistance to treeing becomes essentially the same as uncrosslinked polyethylene.

The prevention of treeing has also been attempted by preparing super clean resin. The inclusion of fillers or decreasing or eliminating the cable's exposure to steam during crosslinking is also helpful.

Silicones have found limited use in the area of anti-treeing. Kato, et al. (U.S. Pat. No. 3,956,420) discloses the use of a combination of ferrocene, in 8-substituted quinoline, and a silicone liquid to increase the dielectric strength of polyethylene and its voltage endurance in water. Ashcraft, et al. (U.S. Pat. No. 4,144,202) inhibits water treeing in ethylene polymer compositions by employing organosilanes containing an epoxy radical. Ashcraft, et al. (U.S. Pat. No. 4,263,158) further discloses the use of organosilanes containing C=N bonds to inhibit water treeing in ethylene polymers. Ashcraft et al. (Canadian Pat. No. 1,103,915) further discloses the use of organosilanes containing C=O bonds to inhibit water treeing in ethylene polymers.

German Offenlegungsschrift Number 2,737,430 and U.S. Pat. No. 4,299,713 disclose the addition of trialkoxysilanes to polyolefin insulation to prevent water tree formation. U.S. Pat. No. 4,332,957 discloses the use of phenoxyalkoxy-substituted silanes as water tree and electrical tree retardant additives. British Pat. No. 1,248,256, and British Pat. No. 1,277,378 disclose treating mineral fillers with organosilanes and then adding them to the polymer to decrease the porosity of the composition. Japanese Patent Number Sho 50[1981]-92946 discloses the use of silicone grafted polyolefins in combination with propionates to inhibit water treeing. Japanese Patent Number Sho 56[1981]-109404 discloses the use of diorganopolysiloxanes having a viscosity range of 30 to 500 centistokes to inhibit water treeing. This patent further discloses siloxanes modified with alkoxy groups have little effect upon water treeing.

As is evidenced by the prior art, treeing can be inhibited in two different ways. If the voids in the plastic are filled, there is slight improvement in resistance to treeing. If voltage stabilizers, such as acetophenone, are included in the polyethylene, the stabilizers are thought to trap and deactivate electrons, and thus inhibit treeing. Most, if not all, of the voltage stabilizers are mobile aromatic compounds. The mobility of the compound, however, can not be so great that it does not stay in the plastic. If the additive is too mobile and low in molecular weight, it migrates to the surface, it evaporates, and its effectiveness is totally lost.

As evidenced by the data in the present application, it is theorized that the ideal composition should contain an additive which is mobile and sufficiently compatible (soluble) with the plastic so it can migrate to the voids and solid impurities which are the points of treeing initiation. By filling and surrounding these faults in the plastic, it retards the initiation of the trees; and by filling the tree channel as it is formed, it retards the growth of the trees. If the additive can fill the tree void and consume or remove the water in the void, the additive would be additionally effective. At the same time, the additive must be sufficiently nonvolatile to assure it stays in the plastic and does not evaporate.

It is a futher object of this invention to provide a composition comprising a polyolefin and a silane anti-treeing additive; the additive being mobile, nonvolatile, and somewhat compatible (soluble) with the plastic. It is a further object of this invention to provide a cable which is manufactured from the compositions of this invention. It is a further object of the invention to provide a method for restoring reliability to underground distribution cable.

SUMMARY OF THE INVENTION

This invention relates to a novel organosilane represented by the general formula

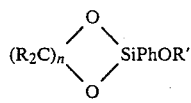

where R denotes a hydrogen atom, or a saturated hydrocarbon radical; n has a value from 2 to 5; Ph represents an aryl radical; and R' represents an alkyl radical with 1 to 6 carbon atoms. The invention also relates to a disiloxane compound made by reacting 2 moles of the aforementioned organosilane (i) with 1 mole of water. This disiloxane compound is represented by the general formula

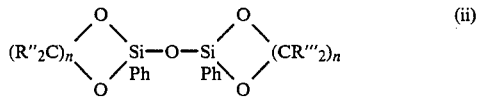

where R" and R'" denote a hdyrogen atom or a saturated hydrocarbon radical, Ph denotes an aryl radical, n has a value from 2 to 5, and at least one R" and at lesat one R'" denotes an alkyl radical with between 1 and 6 carbon atoms on the carbon atoms bonded to the oxygen atoms of this anti-treeing additive.

The invention further relates to improved electrical insulation materials, and to a method for restoring underground residential distribution cables to greater reliability.

DETAILED DESCRIPTION OF THE INVENTION

This invention relates to a novel organosilane compound represented by the general formula

where R denotes a hdyrogen atom, or a saturated hydrocarbon radical and at least one R bonded to an oxygen bonded carbon denotes a saturated hydrocarbon; n has a value form 2 to 5; Ph represents an aryl radical and R' represents an alkyl radical with 1 to 6 carbon atoms. The invention also relates to a novel disiloxane compound made by reacting 2 moles of the aforementioned anti-treeing additive (i) with 1 mole of water. This disiloxane is represented by the general formula

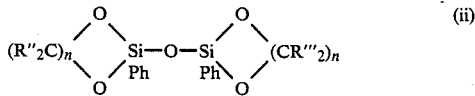

where R" and R'" denote a hydrogen atom or a saturated hydrocarbon radical, Ph denoted an aryl radical, n has a value from 2 to 5, and at least one R" and R'" situated on the carbon atoms bonded to the oxygen atoms of the general formula denotes an alkyl radical with between 1 and 6 carbon atoms.

The novel organosilane (i) is made by combining one mole of an aliphatic diol with one mole of arltrialkoxysilane, or arylalkyltrialkoxysilane and heating the mixture while removing the alcohol generated by the reaction of the alkoxy group of the silane with the diol. Specific aryltrialkoxysilanes which can be used in the synthesis of the anti-treeing additive include, but are not limited to, phenyltrimethoxysilane, phenyltriethoxysilane, phenyltrimethoxyethoxysilane, naphthyltrimethoxysilane, and specific arylalkyltrialkoxysilanes include, but are not limited to 2-phenylpropyltrimethoxysilane, and the like.

The aliphatic diols used in the synthesis of the organosilane (i) are represented by the general formula

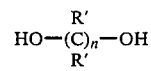

where R' independently denotes either a hydrogen atom or a monovalent hydrocarbon radical with 1 to 6 carbon atoms. It is preferred that at least one of the hydroxyl radicals of the diol be sterically hindered. Preferably, at least one of the R' radicals bonded to at least one of the hydroxyl bonded carbon atoms should be a hydrocarbon radical. Steric hindrance of the oxygen atom is important in stabilizing the cyclic molecule formed by the reaction of the diol with the hydrolyzable groups of the silane. Therefore, it is even more preferred that at least one of the oxygen bonded carbon atoms have two alkyl R' radicals attached thereto. The oxygen atoms of the aliphatic diols can also be hindered by hydrocarbon substitution on carbon atoms adjacent to the oxygen bonded carbon atom. Specific aliphatic diols which can be used in the synthesis of the anti-treeing additives of this application include, but are not limited to, 2-methyl-2,4-pentanediol, 2,3-butanediol, 2,3-diemthyl-2,3-butanediol, 7,8-tetradecanediol, 3,3-dicarbinolheptane, 2,2,4-trimethyl-1,3-pentanediol, 2-ethyl-1,3-hexanediol.

Synthesis of organosilane (i) can be accomplished, for exmaple, by heating equimolar portions of aryltrialkoxysilane and aliphatic diol in the presence of a hydrolysis condensation catalyst such as KOH. The reaction produces an alcohol which can be removed to drive the reaction further to completion. The monocyclic compounds described by formula (i) are liquids which allows them to be easily intermixed with polyolefin polymers, and copolymers of olefins to produce stable anti-treeing thermoplastic materials.

The disiloxane compounds represented by formula (ii) are synthesized, for example, by heating equimolar portions of aryltrialkoxysilane and aliphatic diol with a half molar portion of water in the presence of a catalyst like KOH. The reaction produces alcohol which can be removed to drive the reaction further to completion. The disiloxane compounds are, in some cases, solids which can also be isolated as supercooled liquids at room temperature. Another method of forming the disiloxane is to react the monocyclic compound (i) with a half molar portion of water by heating in the presence of a catalyst.

The aryltrialkoxysilane and aliphatic diols ued in the synthesis of the anti-treeing compounds of the present invention are commercially available materials.

Both the organosilanes (i) and disiloxanes (ii) of the present application can be incorporated into polymeric materials to form improved tree resistant insulation materials. These insulation materials comprise a polyolefin and the compounds of the present invention, either (i) or (ii), which act as anti-treeing additives.

In general, the polymeric component, used in the insulating material can be any solid synthetic organic polymeric resin including polyolefins and copolymers thereof. The polyolefins include solid polymers of olefins, particularly alpha-olefins, which comprise from about two to about six carbon atoms, e.g., crosslinkable and noncrosslinkable polyethylene, polypropylene, polybutene, polyisobutylene, poly(4-methyl pentene), and the like. Copolymers of ethylene, and other compounds interpolymerizable with ethylene such as butene-1, pentene-1, propylene, styrene, and the like, may be employed. In general, the copolymer will be comprised of 50 percent by weight or more of ethylene.

Suitable examples of olefin-vinyl copolymers include copolymers of ethylene-vinyl acetate, ethylene-vinyl propionate, ethylene-vinyl isobutyrate, ethylene-vinyl alcohol, ethylenemethyl acrylate, ethylene-ethyl acrylate, ethylene-ethyl methacrylate, and the like. In general, the ethylene constitutes at least 25 percent by weight of the copolymer.

Specific examples of the suitable olefin-allyl copolymers include copolymers of the ethylene-allyl benzene, ethylene-allyl ether, and ethylene-acrolein. It is preferred, however, that the polymer be a polyolefin, with polyethylene being most preferred.

As far as is known at this time, the order of mixing the components and the specific procedure employed is not critical for the purpose of this invention. The components may be mixed on a variety of apparatus including multi-roll mills, screwmills, continuous mixers, compounding extruders, and Banbury mixers.

The treeing resistance of the plastic is affected by the amount of anti-treeing additive present. The amount of additive used is determined by at least three factors:

1. The level of tree resistance desired-normally this would be as high as possible.
2. The physical properties of the composition Excessive silicone could result in a composition with insufficient integrity for the application. Excessive silicone could also adversely affect the molding process by causing slippage.
3. The economics of the composition - the more silicone that is used the more expensive the composition. Based on these factors, it is recommended the insulation composition contain between 0.1 and 5 percent of the anti-treeing additive, with 0.1 to 4 percent preferred. Most preferrably the anti-treeing additives should comprise between 0.5 and 2 percent.

Minor amounts of other additives may also be employed in conventional amounts to obtain the desired results.

The invention also relates to a method for restoring unreliable underground electrical power distribution cables to more reliable conditions. Such cables can be restored by supplying the liquid monocyclic anti-treeing additives represented by formula (i), or the supercooled liquid form of the disiloxane (ii) to the inner cavity of a stranded wire conductor of such underground cables. The stranded portion of such cables has voids between the multiple strands of wire which will allow the fluid to penetrate the length of the cable. By pressurizing the fluid the anti-treeing additive is supplied to the length of the cable and permeates into the insulation material. Once absorbed into the insulation the anti-treeing additive fills the void spaces of trees and retards their further growth. The permeating fluid may also comprise a hydrolysis condensation catalyst in order to promote reaction with water. Such catalysts include tetraorganotitanates and organotin compounds, and are well known in the art. Alternately, the interstices of the cable can be supplied with the liquid compound (i), or the supercooled liquid form of (ii) of the present invention before being put into service, i.e., the anti-treeing liquid can be supplied during manufacture of the cable. The cable can also be supplied with the anti-treeing compound (i) after installation of the cable is complete.

It is believed that the anti-treeing additives of the present invention act as tree retardant agents due not only to their alkoxy functionality, but also because of the aryl radical on the silicon atom. It is believed that the aryl radical absorbs the electrical stress associated with tree formation.

Alkoxy functionality is thought to retard treeing by hydrolyzing the water associated with water trees. The ring formed by the aliphatic diol in the additives of the general formula (i) of this invention controls the rate of hydrolysis of the alkoxy radical, and thus provides more durable retardancy than conventional alkoxy silanes provide. However, the anti-treeing additives of the general formula (ii) do not hydrolyze at all. Therefore, their activity as anti-treeing additives is not related to alkoxy functionality.

The following examples demonstrate the effectiveness of the invention and aid those skilled in the art to better understand the invention. The following examples should not be udnerstood as delineating the full scope of the invention.

EXAMPLE 1

One mole of phenyltrimethoxysilane and one mole of 2-methyl-2,4-pentanediol were heated in the presence of KOH which catalyzed the exchange of the methoxy groups with the pentanediol. The reaction generated methanol which was distilled off. A fluid was flash-distilled off between 110° C. and 120° C. at about 1 mm Hg, and collected. This fluid had a viscosity of 6.7 cs at 25° C. The compound formed was represented by the general chemical formula

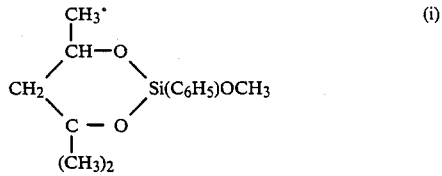

The NMR spectrum of this liquid was consistent with this structure.

EXAMPLE 2

One mole of phenyltrimethoxysilane, one mole of 2-methyl-2,4-pentanediol, and one-half mole of water were heated in the presence of KOH. A solid with a melting point of approximately 104° C. was obtained. The solid could be melted and then supercooled to form a liquid with a viscosity of 700cs at 25° C. This compound is represented by the general chemical formula. The NMR spectrum of the supercooled liquid form of this compound was consistent with this structure.

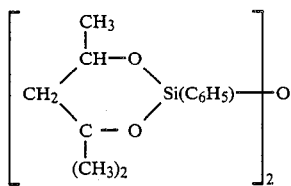

EXAMPLE 3

Compound (i) was used to surface coat beads of thermoplastic polyethylene, USI31006 sold by United States Industries. The treatment level of the beads was 2 percent by weight. The treated beads were compounded using a twin screw extruder which yielded dry beads following processing of the extrudate. Analysis by atomic absorption indicated that the beads contained 1 percent by weight of the silicone compound.

This modified polyethylene was compressed into quarter inch thick slabs with 25 pinpricks. The pinpricks were made by precision needles sold by the Ogura Jewel Industry Company Ltd., 7-12 Omori Kita 5 Chome, Otu-ku, Tokyo 143 Japan. The precision needles had a point radius of five microns and projected into themold 0.125 inches. One inch disks which contained one of the precision pinpricks were cut using a one inch diameter punch. Each sample disk was fastened to 1.5 inch lengths of 0.75 inch diameter PVC pipe with the pinhole of the disk oriented towards the interior portion of the PVC pipe. The bottom of the disk, the portion outside of the cylinder, was spray coated with conductive paint. 10 drops of Triton x100 were dissolved in a pint of water, and 10 μl of this solution wre added to the cylinder formed by the the PVC pipe and the sample disk. The cylinder was filled with saturated aqueous sodium chloride solution and the disk was subjected to 5,000 volts at 3 kHz for 150 hours. This test procedure was repeated using untreated USI31006 polyethylene.

The sample disks were removed from the PVC pipe, dyed with methylene blue, and microtomed. The microtomed slice containing the tip of the precision pinprick was stored in aqueous methylene blue solution. The length of the trees were measured for each sample and the average for each type of polyethylene was computed. The results are reported in Table 1.

TABLE 1

| Material | Test Time | No. of Samples | Tree Length (mm) |
|---|---|---|---|
| USI31006 Resin Untreated | 150 hrs. | 36 | 10.1 ± 1.5 |
| USI31006 Resin with 1% Compound (i) | 150 hrs. | 33 | 4.7 ± 0.3 |

The results demonstrate that polyethylene compounded with the monocyclic anti-treeing additive (i) is less susceptible to water treeing than the untreated resin.

EXAMPLE 4

The disiloxane compound (ii) was compounded with a crosslinkable polyethylene resin, XD 60007.06, made by Dow Chemical Company, Midland, Mich., U.S.A. The resulting treated resins were crosslinked by heating the resin for 10 minutes at 200° C. The peroxide decomposition products which affect tree growth were removed by heating the sample disks at 75° C. for 48 hours. The additive was compounded at about 1.4 weight percent and 2.8 weight percent levels. The tree retardancy of the sample disks was measured using the method described in example 3 except the disk samples were subjected to the electrical stress for 120 hours rather than for 150 hours. Samples of UCC TM 4202, a crosslinkable tree retardant polyethylene available from Union Carbide Corporation of Danbury, CT was tested for its tree retardancy using the same methods. The results of these tests are reported in Table 2.

TABLE 2

| | TREE RETARDANCY | |
|---|---|---|
| Material | No. of Samples | Tree Length (mm) |
| XD 60001.607 | 43 | 10.3 ± 0.7 |
| XD 60001.607 + 1.4% (ii) | 40 | 3.0 ± 0.4 |
| XD 60001.607 + 2.8% (ii) | 45 | 3.7 ± 0.4 |
| UCC 4202 | 39 | 3.2 ± 0.2 |

These results show that the disiloxane anti-treeing additive (ii) operates as an effective tree retardant at 1.4 and 2.8 weight percent. The degree of tree retardance of the (ii) is equivalent in the tests performed to the commercially available product UCC 4202.

EXAMPLE 5

Stranded underground distribution cable was aged by immersing the cable in water and passing high voltage, alternating current through the cable until its breakdown voltage decreased from 180 volts/millimeter to 80 volts/millimeter. Dry nitrogen gas was pumped through the inner stranded portion of the cable for four weeks and the cable's breakdown voltage increased to 98 volts/millimeter.

A 50/50 weight mixture of acetophenane and the organosilane compound of Example 1 was supplied to the inner portion of the nitrogen dried, aged cable. After 6 weeks the breakdown voltage of the cable (A) was 108 volts/millimeter. After 12 weeks the breakdown voltage was 122 volts/millimeter.

The same procedure using the organosilane of Example 1 alone increased the breakdown voltage of the nitrogen-dried, aged cable from 98 volts/millimeter to 120 volts/millimeter after 6 weeks of treatment with the organosilane.

EXAMPLE 6

Condensation catalysts were added to the organosilane compound of Example 1 at room temperature and in the presence of atmospheric moisture. The mixtures were characterized periodically over ten days for changes in viscosity, and for changes in chemical composition. In particular, the relative amounts of the starting material (the organosilane) and the reaction product (the disiloxane of Example 2) were measured by gas chromatography. The results are reported in Table 3. The condensation catalysts were added at about 0.1 weight percent levels.

TABLE 3

| | Viscosity (centistokes at room temperature) | | Area % Product (disiloxane) | |
|---|---|---|---|---|
| Catalyst | Initial | 7 Days | Initial | 7 Days |
| DBTL* | <5 | 355 | 0 | 82% |
| TIPT** | <5 | 730 | 0 | 80% |

TABLE 3-continued

| Catalyst | Viscosity (centistokes at room temperature) | | Area % Product (disiloxane) | |
|---|---|---|---|---|
| | Initial | 7 Days | Initial | 7 Days |
| None | <5 | 15 | — | — |

*DBTL - dibutyltindilaurate
**TIPT - tetraisopropyltitanate

This indicates that the organosilane mixture of Example 1 can be mixed with a condensation catalyst, and injected into the center conductor cavity of a stranded cable to form a viscous fluid or solid in said cavity.

What is claimed is:

1. An improved electrical cable insulation material comprised of
   (a) polyolefin
   (b) an anti-treeing additive chosen from the group consisting of
   (i) a compound represented by the general formula

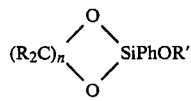

where each R independently denotes a hydrogen atom, or a saturated hydrocarbon radical; n has a value from 2 to 5; Ph represents an aryl radical; and R' represents an alkyl radical with 1 to 6 carbon atoms; and
   (ii) a compound represented by the general formula

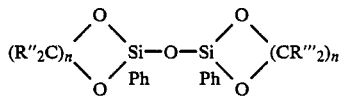

where R″ denotes a hydrogen atom or a saturated hydrocarbon radical, Ph denoted an aryl radical, n has a value from 2 to 5, and at least R″ and one R‴ radical on the oxygen bonded carbon atoms of said general formula denotes an alkyl radical with between 1 and 6 carbon atoms; wherein the polyolefin (a) and the anti-treeing additive (b) are intermixed, and the anti-treeing additive comprises between 0.1 and 5 weight percent of the improved cable insulation material.

2. The improved electrical cable insulation of claim 1 wherein the polyolefin is noncrosslinked polyethylene, cross-linked polyethylene, polypropylene, or poly(ethylene copropylene) rubber.

3. The improved electrical cable insulation of claim 2 wherein the anti-treeing additive is present between 0.1 and 4 weight percent of said improved electrical cable insulation.

4. The improved electrical cable insulation of claim 3 wherein the anti-treeing additive is present between 0.5 and 2 weight percent of said the improved electrical cable insulation.

5. A method for restoring aged undependable electrical cables which comprises providing a fluid comprised of a compound represented by the general formula

where R denotes a hydrogen atom, or a saturated hydrocarbon radical; n has a value from 2 to 5; Ph represents an aryl radical; and R' represents an alkyl radical with 1 to 6 carbon atoms to the center cavity of a stranded wire conductor distribution cable having polyolefin insulation.

6. The method of claim 5 wherein the fluid further comprises a hydrolysis condensation catalyst.

7. A method of rendering electrical cable resistant to electromechanical treeing comprising the step of providing a fluid comprised of a compound represented by the general formula

where R denotes a hydrogen atom, or a saturated hydrocarbon radical; n has a value from 2 to 5; Ph represents an aryl radical; and R' represents an alkyl radical with 1 to 6 carbon atoms to the center cavity of a stranded wire conductor distribution cable having polyolefin insulation.

* * * * *